United States Patent [19]

Takada et al.

[11] Patent Number: 4,636,381

[45] Date of Patent: Jan. 13, 1987

[54] COATED UBIDECARENONE-CONTAINING LIPOSOME

[75] Inventors: Masahiro Takada; Teruaki Yuzuriha; Kouichi Katayama, all of Ibaraki; Junzo Sunamoto, Nagasaki, all of Japan

[73] Assignee: Eisai Co., Ltd., Tokyo, Japan

[21] Appl. No.: 497,255

[22] Filed: May 19, 1983

[30] Foreign Application Priority Data

May 19, 1982 [JP] Japan ................................. 57-82993

[51] Int. Cl.$^4$ ........................... A61K 9/10; A61K 9/52
[52] U.S. Cl. ........................................ 424/38; 424/14; 424/35; 424/88
[58] Field of Search ................. 424/14, 38, 88, 199, 424/35

[56] References Cited

U.S. PATENT DOCUMENTS 4,310,505  1/1982  Baldschwiller ..................... 252/319

FOREIGN PATENT DOCUMENTS 58-49311  3/1983  Japan.

OTHER PUBLICATIONS

Alonso et al, "On the Interaction of Ubiquinones with Phospholysed Bilayers", Febs. Letters, vol. 132(1), 19–22 (1981).
CA 97:77151d, CA 93:90638m, CA 91-78768.

Primary Examiner—Albert T. Meyers
Assistant Examiner—C. Joseph Faraci
Attorney, Agent, or Firm—Wenderoth, Lind & Ponack

[57] ABSTRACT

A coated ubidecarenone-containing liposome which comprises the ubidecarenone-containing liposome and a polysaccharide fatty acid ester applied on the surface of the membrane of said liposome, whereby the ubidecarenone can be selectively transferred in high concentrations to the lungs, spleen and kidneys.

2 Claims, 4 Drawing Figures

COATED UBIDECARENONE-CONTAINING LIPOSOME

BACKGROUND OF THE INVENTION

1. Field of the Invention

This invention relates to a coated ubidecarenone-containing liposome comprising the ubidecarenone-containing liposome and a polysaccharide fatty acid ester applied on the membrane of the liposome.

2. Description of the Prior Art

Ubidecarenone, also known as coenzyme $Q_{10}$, has recently come into widespread clinical use as a medicine effective for improving the function of the heart.

There is still room for improvement in the speed of transfer of this substance from the blood to a target organ in intravenous or oral administration. This is the reason why, if this substance is for instance formed into a pharmaceutical preparation in accordance with a conventional technique and administered, the speed of its disappearance from the blood is considerably low, and therefore the speed of its transfer to the target organ and the amount transferred are reduced.

Since ubidecarenone is a normally solid lipid-soluble substance having a melting point of 48° to 52° C., it must be solubilized by a conventional technique involving the use of a surfactant such as HCO (polyoxyethylene-hardened castor oil) in order to render it convenient for intravenous administration. However, if it is administered in the thus solubilized state, the speed of disappearance of ubidecarenone from the blood is low, and the speed of its transfer in the initial stage after administration to the heart, spleen and liver, i.e., the target organs, especially to the heart, is low.

SUMMARY OF THE INVENTION

In view of the above background, the present inventors have made various investigations to discover a ubidecarenone-containing composition which is effective for increasing the transfer of ubidecarenone from the blood to predetermined target organs. These investigations have led to the discovery that such a composition can be provided by incorporating ubidecarenone in liposome, on the basis of which there was filed copending U.S. patent application Ser. No. 396,095 filed July 7, 1982, entitled "Ubidecarenone-Containing Liposome".

Experimental Examples given in the above-mentioned Application show that after administration of the ubidecarenone-containing liposome, the speed of disappearance of ubidecarenone from the blood was much higher, and the amount of ubidecarenone transferred within a predetermined time period to organs except the lungs and kidneys was larger, as compared with the case of administering the solubilized ubidecarenone prepared in accordance with the conventional technique.

As is well known in the medical and pharmacological field, it has come to be regarded, with gradually increased interest, important to develop a technique which uses liposome as a means to provide a medicine of the so-called, organoavailability type. Thus, in view of the fact that the liposomes are contained in the respective organs as the inherent liposomes, there have been techniques developed which intend to selectively and concentrically transfer the medicine to the target organ by administering a given medicine contained in a given liposome.

There are exemplified Japanese Patent Application KOKAI(laid-open) Nos. 143,218/77; 151,718/77; 133,616/78; and Japanese Patent Publication No. 8,488/80, for example. These disclosures all relate to techniques to hold a specific organism or medical component on a liposome as a carrier. These techniques are expected, before long, to apply to other organism or medical components in the medical or pharmacological field.

In the U.S. Application Ser. No. 396,095 a novel ubidecarenone-containing liposome is produced by applying the liposome technology, whereby the aforesaid basic problems of ubidecarenone are solved and the utilitarian merit of ubidecarenone is greatly increased.

We further studied a method for producing ubidecarenone having a selective organoavailability against, especially, lungs and kidneys, taking into consideration the fact that the organoavailability of the ubidecarenone varies depending on the physico chemical properties. As a result, we found that the desired purpose is accomplished by coating the ubidecarenone-containing liposome with a polysaccharide fatty acid ester to form a coated ubidecarenone-containing liposome. This invention is based on such discovery.

The object of this invention therefore is to provide a coated ubidecarenone-containing liposome for improvement of the speed of transfer of the ubidecarenone from the blood to a target organ such as lungs and kidneys.

DETAILED DESCRIPTION OF THE INVENTION

Figure 1:
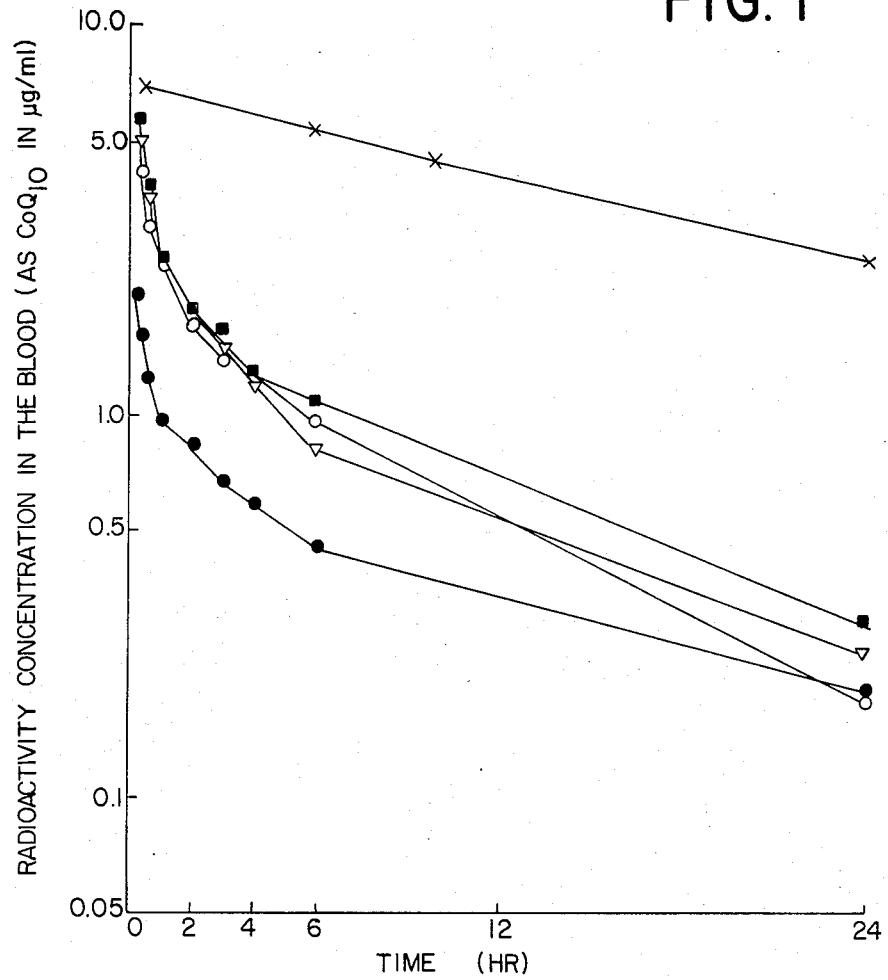
FIG. 1 is a graphic representation showing the results obtained in Experimental Example 1, concerning the speed of disappearance of ubidecarenone from the blood.

In the liposome according to this invention, ubidecarenone is contained in a membrane constituting the liposome. The liposome is mainly composed of a phospholipid and a sterol. Ubidecarenone is present together with these substances, and is dispersed uniformly within the membrane.

Examples of the phospholipid used in this invention are phosphatidyl choline, phosphatidyl ethanolamine, phosphatidyl serine, sphingomyelin, dicetylphosphoric acid, stearylamine, phosphatidyl glycerol, phosphatidic acid, phosphatidyl inositol and mixtures thereof. It is however not specifically limited to these species. With reference to the sterol, cholesterol is most preferable.

The proportions of ubidecarenone, the phospholipid and the sterol in the liposome are such that at least 10 moles of the phospholipid and at least 1 mole of the sterol are present per mole of ubidecarenone. For example, per mole of ubidecarenone, the proportion of the phospholipid is preferably 10 to 30 moles if it is egg yolk phosphatidyl choline, and the proportion of the sterol is preferably 1 to 10 moles if it is cholesterol.

Preferred proportions in moles of various phospholipids and cholesterol per mole of ubidecarenone are shown in the following table.

| Examples    | 1  | 2  | 3  | 4  | 5 | 6 | 7  |
|-------------|----|----|----|----|---|---|----|
| Phospholipid|    |    |    |    |   |   |    |
| PC          | 10 | 15 | 18 | 12 | 5 | 9 | 20 |
| DCP         |    |    |    | 2  |   |   | 5  |
| PS          |    |    |    |    | 5 |   |    |
| SA          |    |    |    |    |   | 1 | 5  |
| Cholesterol | 5  | 5  | 4  | 4  | 5 | 5 | 5  |

PC: phosphatidyl choline
DCP: dicetylphosphoric acid
PS: phosphatidyl serine
SA: stearylamine The liposome of this invention, when observed under an electron microscope, is a spherical particle having a particle diameter of about 0.1 to 5.0μ. Its lyophilized product is aggregated and in appearance is in the form of block. When put into water or salt solutions, it disperses well to give a homogeneous solution.

The liposome of this invention can be produced substantially in accordance with the conventional technique for the production of liposome. For example, it can be produced by charging a membrane-constituting component of the liposome and ubidecarenone into an eggplant-shaped flask, adding chloroform to dissolve these substances, then evaporating the solvent, peeling the resulting membrane by adding a glass bead and a suitable buffer etc., ultrasonicating the resulting solution, passing the treated solution through a column of Sephadex or Sepharose, collecting liposome fractions, and removing the solvent. The removal of the solvent can be effected by, for example, lyophilization.

If the lyophilization is carried out for at least 3 hours under a pressure of not more than 2.0 torr, the intended object of this invention can be achieved and the liposome can be taken out as a powder. The invention, however, is not limited to these specific conditions. As shown in a working example to be given hereinbelow, the lyophilization is desirably carried out for 5 hours under a pressure of 0.3 torr, for example.

In the polysaccharide fatty acid ester according to this invention, the term "polysaccharide" refers to those having a molecular weight of more than 40,000. Dextran, amylopectin and pullulan are practically preferable polysaccharides in this invention and the other polysaccharides such as dextran sulfuric acid, chiotic acid, pullulan sulfuric acid and the like also can be used. In this invention, the polysaccharide may be used as a combination of polysaccharides, such as a combination of two or more polysaccharides having different molecular weights, or a combination of amylopectin and dextran.

The fatty acid component of the polysaccharide fatty acid ester according to this invention is lauric acid, myristic acid, palmitic acid, or stearic acid. Palmitic acid is particularly preferable. When liposome is coated with the polysaccharide fatty acid ester according to this invention, it is assumed that the alkyl chain of the fatty acid will orient to the lipid layer of liposome in a wedge form. It is therefore concluded that the above fatty acid is especially preferable, because the length of the alkyl chain is suitable for the wedge-shaped orientation to the lipid layer of the liposome.

The polysaccharide fatty acid ester may be generally prepared, as follows:

A polysaccharide is first dissolved in dimethyl formamide anhydride with heating at 60° C. to 70° C.

Another solution is prepared by dissolving a fatty acid chloride in pyridine anhydride and dimethylformaide anhydride. The solution is added to the above polysaccharide solution.

This reaction mixture is stirred for several hours at 60° C. to 70° C., and for an additional 24 hours at room temperature. After the reaction is completed, ethanol is added to the reaction mixture to deposit white preciptates. These preciptates are recovered by filtration, followed by washing with ethanol. The precipitates are dispersed in ether, and again filtered to recover them. The recovered product is dried under reduced pressure to provide the intended ester.

The resulting ester can be identified with IR spectrum (KBr method), and $H^1$-NMR spectrum (solvent: $d^6$-DMSO, internal standard substance: TMS). Further, the substitution degree of the fatty acid can be determined.

The substitution degree of the fatty acid means the number of fatty acid molecules introduced into 100 saccharide units. The number is determined with the $H^1$-NMR spectrum method.

For example, when the palmitoyl group is introduced, the amount of the fatty acid introduced is given by the ratio between the peak area appearing at 0.9 ppm and 1.28 ppm of the $H^1$-NMR spectrum due to the protons in the palmitoyl groups and the peak area appearing in the range of 3.5 to 5.2 ppm due to the protons in the saccharides. More particularly, when x is the number of pamiltoyl groups substituted in 100 saccharide units, the number of protons in the saccharides is given as $9x+10(100-x)$; and the number of protons in the palmitoyl groups is given as $31x$. Therefore, assuming that y is the number of protons in the saccharides obtained from an integral curve of the $H^1$-NMR spectrum, and z is the corresponding number of the palmitoyl groups, the following equation is given:

$$x = \frac{1000z}{31y + z}$$

The data of such substitution degree are applied to the esters to be used in this invention. Better results are shown in the lower substitution degree. For example, sufficient results are provided at the level of substitution of 0.5 to 5.

Coating of the liposome with the ester of this invention may be achieved by adding an aqueous ester-containing solution to the aqueous solution composed of the liposome, followed by stirring. In coating, there may be used a single ester, or a combined ester comprising two or more esters according to this invention.

The following experimental examples illustrate the effect of the coated ubidecarenone-containing liposome of this invention.

EXPERIMENTAL EXAMPLE 1

Sample

The following assay samples a–d were prepared by the same method as described in Examples 1 to 3, except that $^{14}C$-$CoQ_{10}$ was used instead of $CoQ_{10}$ described in Examples 1 to 3:

(a) A liposome containing $^{14}C$-$CoQ_{10}$.

(b) A coated liposome containing $^{14}C$-$CoQ_{10}$; the ester for coating is O-palmitoyl amylopectin (molecular weight: 112,000—substitution degree of fatty acid: 4.9).

(c) A coated liposome containing $^{14}C$-$CoQ_{10}$: the ester for coating is O-palmitoyl pullulan (molecular weight: 50,000—substitution degree of fatty acid: 3.4).

(d) A coated liposome containing $^{14}C$-$CoQ_{10}$: the ester for coating is O-palmitoyl pullulan (molecular weight; 230,000—substitution degree of fatty acid: 1.0).

A control sample (sample e) was obtained by adding HCO-60 to $^{14}C$-$CoQ_{10}$, the amount of the former being four times that of the latter, and subjecting the solution to ultrasonication, to provide solubility and adding physiological saline to a concentration of 0.6 mg/ml. The expression, $^{14}C$-$CoQ_{10}$ is a radiation-labelled ubidecarenone represented by the following formula:

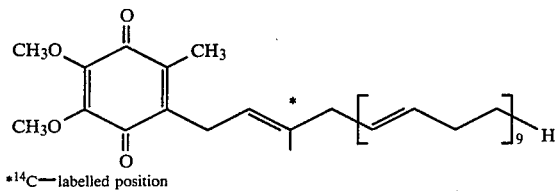

*$^{14}C$—labelled position

This compound had a relative radioactivity of 48 $\mu Ci/mg$, and its radiochemical purity was observed by thin layer chromatography using two types of developing solvent (chloroform/benzene=1/1; acetic acid/benzene=1/9).

Procedure

1. Animal experiment

The assay sample was injected in an amount of 0.6 mg/kg as $^{14}C$-$CoQ_{10}$ into the left femoral vein of male guinea pigs (body weight 300–350 g), followed by suturing. The control sample was administered at the same dose in the same manner. The animals were then left in a cage, and blood was drawn from the ear vein every predetermined period of time. The concentration of $^{14}C$-$CoQ_{10}$ in the blood was measured by the following method.

2. Measurement of radioactivity in the blood

20 $\mu l$ or 50 $\mu l$ of blood was taken from the ear vein, and solubilized with 0.75 ml of Soluene 350/isopropyl alcohol (1/1). Several drops of aqueous hydrogen peroxide were added to decolorize the solution. Then, 5 ml of instagel/0.5N HCl (9/1) was added, and radioactivity was measured by means of a liquid scintillation counter.

3. Results

FIG. 1 shows the variation with time in the radioactivity concentration of $^{14}C$-$CoQ_{10}$ in the blood after the administration of the assay sample or the control sample.

In FIG. 1, the curves plotted by the marks ○, ●, ■, ▽, and × exhibit the variations (average of two runs) after the administration of the samples a, b, c, d and e, respectively.

It was already confirmed in the invention of U.S. patent application Ser. No. 396,095 that the ubidecarenone contained in liposome rapidly disappears from the blood and is transferred to the organs; this is shown in FIG. 1. This phenomenon still existed even when the surface of the membrane of the liposome is coated with a polysaccharide fatty acid ester. In some cases, the speed of disappearance in the blood may be rather accelerated by coating.

EXPERIMENTAL EXAMPLE 2

Samples

The same assay sample and control sample as described in Experimental Example 1 were used.

Procedure

1. Animal experiment

Each of the above samples was injected in a dose of 0.6 mg/kg into the left femoral vein of male guinea pigs (body weight 300 g–350 g) and suturing was performed. The animals were then left in a cage. After 24 hours from the administration, the animals were killed by decapitation, and the organs were removed. In order to prevent contamination of the brain and heart by blood, physiological saline was circulated from the left ventricle to the jugular vein to draw the blood, and then the brain and heart were removed.

2. Measurement of radioactivity in the tissues

About 100 mg of each organ was added to 0.5 ml of Soluene 350, and incubated at 50° C. for 2 hours to dissolve the tissues. Then, 6 ml of instagel/0.5N HCl (9/1) was added, and radioactivity was measured by using a liquid scintillation counter.

3. Results

After 24 hours from the intravenous injection of $^{14}C$-$CoQ_{10}$ in the assay sample and $^{14}C$-$CoQ_{10}$ in the control sample, the concentrations of radioactivity in the main organs were expressed in terms of $CoQ_{10}$, and the transfer of the former to the organs was compared with that of the latter. The results are shown in FIGS. 2 to 4.

Figure 2:
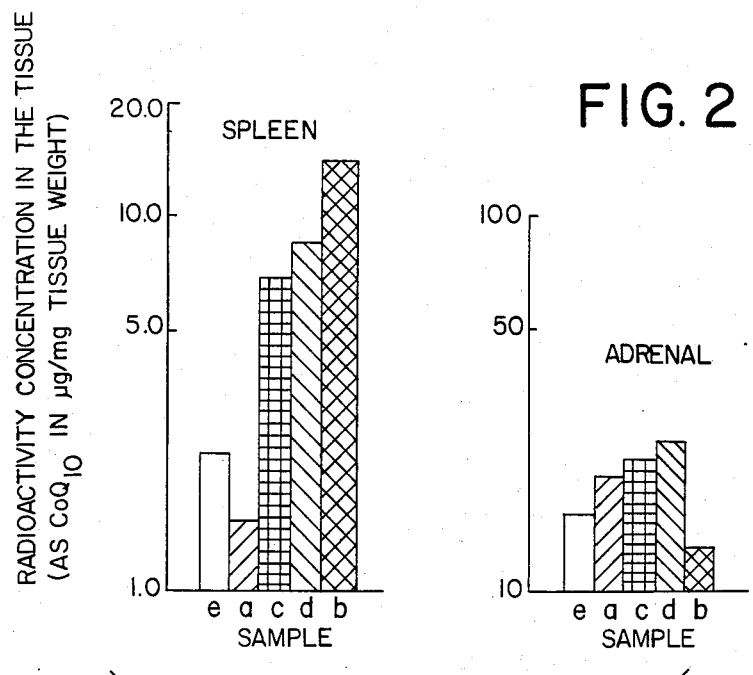
FIGS. 2 to 4 are graphic representations showing the results obtained in Experimental Example 2, concerning the transfer distribution of ubidecarenone to the respective organs.
Figure 3:
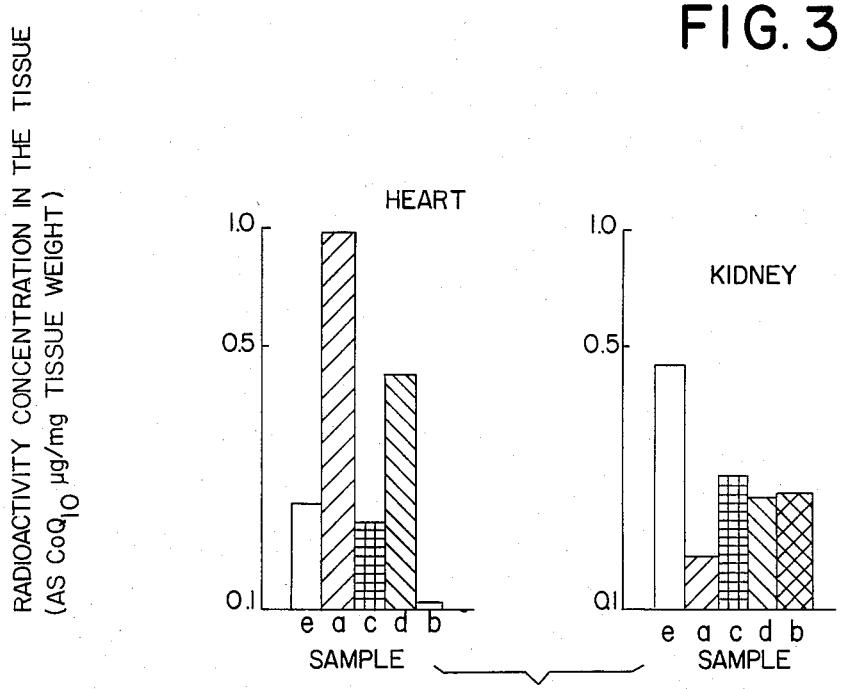
Figure 4:
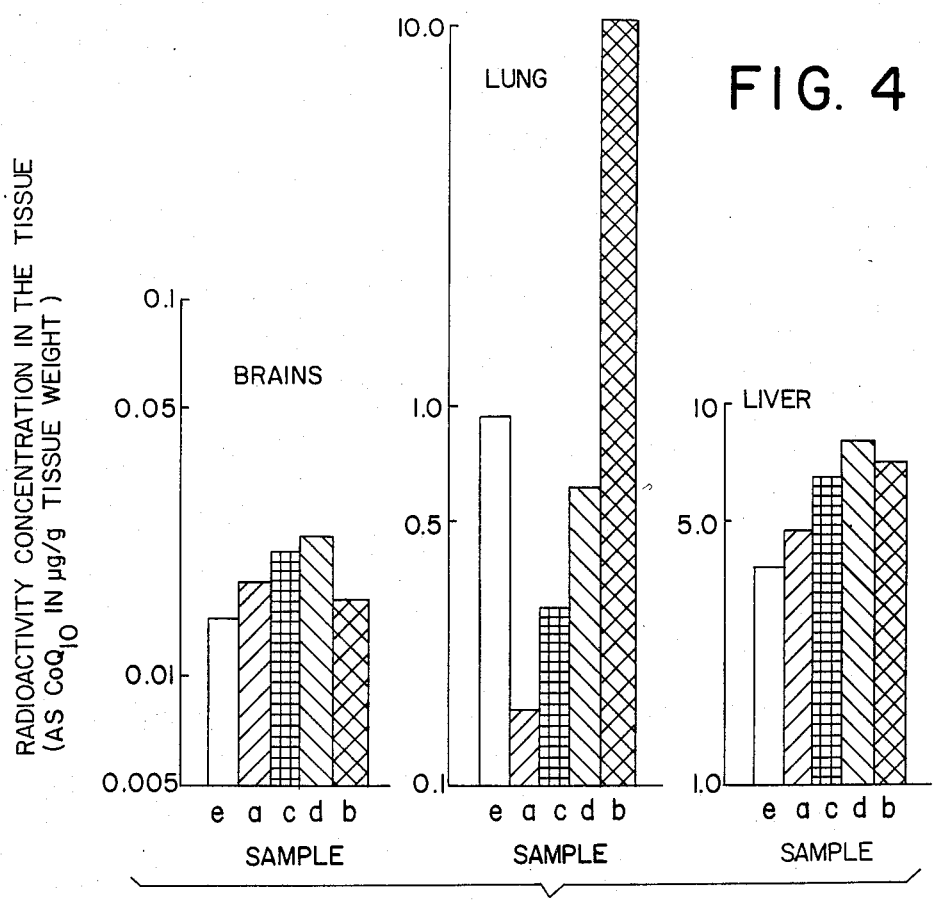

In FIGS. 2 to 4, the respective columns ▨, ▧, ⊞, ▦ and ☐ show the amounts of the sample a, b, c, d and e transferred to the organ.

As shown in FIGS. 2 to 4, and as confirmed in the invention of U.S. patent application Ser. No. 396,095, the ubidecarenone contained in liposome is rapidly distributed in the brain, heart, liver, spleen and adrenal gland in high concentrations. It is observed that when the membrane surface of the liposome is further coated with polysaccharide fatty acid ester, the ubidecarenone is distributed in the respective organs of lungs, spleen and kidneys in high concentrations. In the comparison of the transfer of the respective samples to the lungs, spleen and kidneys, it is recognized that the sample c versus the sample a is distributed at the concentration as high as 1.8 times, 4.7 times and 1.6 times, respectively. Similarly, the sample d versus the sample a is distributed at the concentration as high as 3.8 times, 5.4 times and 1.4 times, respectively. The sample b versus the sample a is distributed at the concentration as remarkabley high as 62.5 times, 8.8 times and 1.4 times, respectively. On the contrary, in the comparison of the transfer of the respective samples to the others organs, it is found that the transfers of the samples b, c and d are equivalent to or less than the transfer of sample a. From the above studies, it was proved that, according to the coated ubidecarenone-containing liposome of this invention, the ubidecarenone can be transferred more selectively to the lungs, spleen and kidneys.

The following Examples more specifically illustrate the present invention.

EXAMPLE 1

36 mg ($4.5 \times 10^{-5}$ mole) of egg yolk phosphatidyl choline, 5.85 mg ($1.5 \times 10^{-5}$ mole) of cholesterol and 2.16 mg ($2.5 \times 10^{-6}$ mole) of ubidecarenone, i.e. $CoQ_{10}$, were dissolved in 2 ml of chloroform. Chloroform was removed under reduced pressure by using a rotary evaporator. The resulting thin film was dried overnight by a desiccator under reduced pressure to remove chloroform completely. One glass bead and 3.0 ml of a buffer A (to be described below) were added twice to the thin film left on the bottom of the flask, and the mixture was shaken by a vortex mixer until the film was completely peeled off.

The solution was then transferred to a branched test tube, and subjected to ultrasonication treatment at 42 W for 53 minutes intermittently every 30 seconds by using a probe-type sonicator in an ice bath under a stream of argon to give a translucent pale yellow solution.

The solution was applied onto a column (1.6×45 cm) of Sepharose 4B, and eluted with the buffer A. Then, 1.8 ml portions of the eluate were taken respectively into 60 test tubes. A fraction which was eluted a little later near the void volume of this column was concentrated to a final volume of 2.3 ml (1.37 mg as $CoQ_{10}$) by means of a polycarbonate membrane having a pore size of 0.03 μm. The resulting liposome had a diameter of 25 to 30 nm by observation under an electron microscope.

The buffer A denotes a 0.01M phosphate buffer (pH 7.4) containing 0.1M NaCl.

Subsequently, 0.2 ml of a solution prepared by dispersing 30 mg of O-palmitoyl amylopectin (molecular weight: 112,000—substitution rate of fatty acid 4.9) in 1.0 ml of buffer solution A was mixed with 0.7 ml of a concentrated liposomal suspension produced as hereinbefore described. The mixture was stirred at room temperature for 30 minutes. A coated ubidecarenone-containing liposome (0.42 mg as $CoQ_{10}$) was thus obtained.

EXAMPLE 2

The same procedure as described in Example 1 was repeated except that O-palmitoyl pullulan (molecular weight: 50,000—substitution rate of fatty acid 3.4) was used in place of O-palmitoyl amylopectin (molecular weight: 112,000—substitution rate of fatty acid 4.9). A coated ubidecarenone-containing liposome (0.42 mg as $CoQ_{10}$) was obtained.

EXAMPLE 3

The same procedure as described in Example 1 was repeated except that O-palmitoyl pullulan (molecular weight: 230,000—substitution rate of fatty acid 1.0) was used in place of O-palmitoyl amylopectin (molecular weight: 112,000—substitution rate of fatty acid 4.9). A coated ubidecarenone-containing liposome (0.42 mg as $CoQ_{10}$) was obtained.

EXAMPLE 4

A 200 ml eggplant-shaped flask was charged with 60.0 mg (3 moles) of egg yolk phosphatidyl choline, 9.8 mg (1 mole) of cholesterol and 6.5 mg (0.3 moles) of ubidecarenone, and 4 ml of chloroform was added to dissolve them. The solvent was evaporated under reduced pressure. Four milliliters of physiological saline and a glass bead were added, and dispersed by using a vortex mixer. The resulting multilayer film was transferred to a branched test tube, and under an atmosphere of nitrogen gas, subjected to ultrasonication treatment at 25 KW for 15 minutes in an ice bath. The solution was then charged onto a column of Sephadex G-50 and eluted with physiological saline as an eluent. Liposomal fractions were collected and diluted to 30 ml. The diluted liposomal fractions were lyophilized for 5 hours under a pressure of 0.3 torr.

The liposome produced was added to 10 ml of an aqueous dispersion of O-palmitoyl amylopectin (molecular weight: 112,000—substitution rate of fatty acid 4.9), and stirred at room temperature for 30 minutes, followed by lyophilizing again. A coated ubidecarenone-containing liposome was obtained.

What we claim is:

1. A coated ubidecarenone-containing liposome which comprises a ubidecarenone-containing liposome and a polysaccharide fatty acid ester coating on the surface of a membrane of said liposome effective to speed the transfer of Ubidecarenone from the blood to a target organ, wherein the membrane of said liposome is composed of, per mole of ubidecarenone, 1–10 moles of cholesterol and 10–30 moles of at least one compound selected from the group consisting of phosphatidyl choline, phosphatidyl ethanolamine, phosphatidyl serine, sphingomyelin, dicetylphosphoric acid, stearylamine, phosphatidyl glycerol, phosphatidic acid and phosphatidyl inositol; the fatty acid component of said polysaccharide fatty acid ester is selected from the group consisting of lauric acid, myristic acid, palmitic acid and stearic acid; the substitution degree of the fatty acid component of said polysaccharide fatty acid ester is 0.5 to 5; and the polysaccharide component has a molecular weight of more than 40,000 and is at least one member selected from the group consisting of dextran, amylopectin, pullulan, dextran sulfuric acid, chiotic acid and pullulan sulfuric acid.

2. The coated ubidecarenone-containing liposome of claim 1 wherein the polysaccharide fatty acid ester is a palmitic acid ester of a polysaccharide selected from the group consisting of amylopectin, pullulan and dextran.

* * * * *